(12) United States Patent
Kwon et al.

(10) Patent No.: US 12,171,563 B2
(45) Date of Patent: Dec. 24, 2024

(54) APPARATUS FOR ESTIMATING BIO-INFORMATION, AND METHOD OF DETERMINING FALSE DETECTION OF BIO-SIGNAL PEAKS

(71) Applicant: SAMSUNG ELECTRONICS CO., LTD., Suwon-si (KR)

(72) Inventors: Ui Kun Kwon, Hwaseong-si (KR); Jae Min Kang, Seoul (KR); Youn Ho Kim, Hwaseong-si (KR); Sang Kon Bae, Seongnam-si (KR); Jin Woo Choi, Ansan-si (KR); Chang Mok Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 130 days.

(21) Appl. No.: 17/970,197

(22) Filed: Oct. 20, 2022

(65) Prior Publication Data

US 2023/0131673 A1 Apr. 27, 2023

Related U.S. Application Data

(63) Continuation-in-part of application No. 17/589,207, filed on Jan. 31, 2022, now Pat. No. 11,896,353.

(30) Foreign Application Priority Data

Oct. 26, 2021 (KR) .................. 10-2021-0143345

(51) Int. Cl.
*A61B 5/349* (2021.01)
*A61B 5/021* (2006.01)
(Continued)

(52) U.S. Cl.
CPC .............. *A61B 5/349* (2021.01); *A61B 5/021* (2013.01); *A61B 5/372* (2021.01);
(Continued)

(58) Field of Classification Search
CPC ....... A61B 5/00; A61B 5/0035; A61B 5/0472; A61B 5/349; A61B 5/352; A61B 5/372;
(Continued)

(56) References Cited

U.S. PATENT DOCUMENTS 6,714,804 B2 3/2004 Al-Ali et al.
8,540,630 B2 9/2013 Hwang et al.
(Continued)

FOREIGN PATENT DOCUMENTS

JP 2010-46284 A 3/2010
KR 10-0498794 B1 7/2006
(Continued)

OTHER PUBLICATIONS

NPL Search (May 8, 2023).*
(Continued)

*Primary Examiner* — Van T Trieu
(74) *Attorney, Agent, or Firm* — Sughrue Mion, PLLC

(57) ABSTRACT

An apparatus for estimating bio-information is provided. The apparatus for estimating bio-information by using an ultrasonic signal according to an embodiment of the present disclosure includes: an ultrasonic sensor configured to acquire an ultrasonic signal from an object; and a processor configured to detect peaks from the acquired ultrasonic signal, and to determine false detection of a peak, among the detected peaks, by using at least one of amplitudes of the detected peaks or a left waveform shape and a right waveform shape of the peak.

20 Claims, 16 Drawing Sheets

(51) Int. Cl.
*A61B 5/372* (2021.01)
*A61B 5/024* (2006.01)
*A61B 8/00* (2006.01)
*A61B 17/00* (2006.01)

(52) U.S. Cl.
CPC ............ *A61B 5/02438* (2013.01); *A61B 8/44* (2013.01); *A61B 2017/0011* (2013.01)

(58) Field of Classification Search
CPC .... A61B 8/00; A61B 8/06; A61B 8/13; A61B 8/42; A61B 8/44; A61B 8/463; G08B 21/00; G08B 21/04; G08B 21/0453; G08B 25/01; G08B 25/016; G08B 25/10
See application file for complete search history.

(56) References Cited

U.S. PATENT DOCUMENTS

| | | | |
|---|---|---|---|
| 9,107,596 | B2 | 8/2015 | Kim et al. |
| 9,675,297 | B2 | 6/2017 | Kim et al. |
| 10,206,620 | B2 | 2/2019 | Camacho Perez et al. |
| 10,744,261 | B2 | 8/2020 | Newberry et al. |
| 10,863,947 | B2 | 12/2020 | Golda et al. |
| 11,020,037 | B2 | 6/2021 | Pan et al. |
| 2006/0025688 | A1* | 2/2006 | Hayase ................. A61B 8/463 600/438 |
| 2010/0168594 | A1 | 7/2010 | Chuang |
| 2012/0259182 | A1 | 10/2012 | Kim et al. |
| 2014/0364732 | A1* | 12/2014 | Lim ......................... A61B 8/02 600/509 |
| 2016/0071391 | A1* | 3/2016 | Chang ................. G08B 21/0453 340/539.12 |
| 2019/0231277 | A1 | 8/2019 | Fischer et al. |
| 2019/0313980 | A1 | 10/2019 | Yoon et al. |
| 2021/0169356 | A1 | 6/2021 | Jang et al. |

FOREIGN PATENT DOCUMENTS

| | | |
|---|---|---|
| KR | 10-2007-0062626 A | 6/2007 |
| KR | 10-2012-0003662 A | 1/2012 |
| KR | 10-2012-0113530 A | 10/2012 |
| KR | 10-1366101 B1 | 2/2014 |
| KR | 10-2018-0021373 A | 3/2018 |
| KR | 10-2018-0037525 A | 4/2018 |
| KR | 10-2019-0051299 A | 5/2019 |
| KR | 10-2019-0120684 A | 10/2019 |
| KR | 10-2020-0024518 A | 3/2020 |
| KR | 10-2020-0091209 A | 7/2020 |

OTHER PUBLICATIONS

Jezewski, Janusz et al., "A novel technique for fetal heart rate estimation from Doppler ultrasound signal", BioMedical Engineering Online, Oct. 14, 2011, vol. 10, No. 1, XP021112035. (17 pages total).

Communication issued Sep. 8, 2022 by the European Patent Office in European Patent Application No. 22163761.4.

Communication issued on Jul. 25, 2024 by the Korean Intellectual Property Office for Korean Patent Application No. 10-2022-0085556.

* cited by examiner

APPARATUS FOR ESTIMATING BIO-INFORMATION, AND METHOD OF DETERMINING FALSE DETECTION OF BIO-SIGNAL PEAKS

CROSS-REFERENCE TO RELATED APPLICATION(S)

This application is a continuation-in-part of U.S. application Ser. No. 17/589,207, filed Jan. 31, 2022, which claims priority from Korean Patent Application No. 10-2021-0143345, filed on Oct. 26, 2021, in the Korean Intellectual Property Office, the entire disclosure of which is herein incorporated by reference for all purposes.

BACKGROUND

1. Field

The disclosure relates to technology for non-invasively estimating bio-information.

2. Description of the Related Art

Recently, with the aging population, soaring medical costs, and a lack of medical personnel for specialized medical services, research is being actively conducted on information technology (IT)-medical convergence technologies, in which IT technology and medical technology are combined. Particularly, monitoring of the health condition of the human body is not limited to medical institutions, but is expanding to mobile healthcare fields that may monitor a user's health condition anywhere and anytime in daily life at home or office. Typical examples of bio-signals, indicating the health condition of individuals, include an electrocardiography (ECG) signal, a photoplethysmogram (PPG) signal, an electromyography (EMG) signal, etc., and various bio-signal sensors have been developed to measure these signals in daily life.

SUMMARY

According to an aspect of an example embodiment of the disclosure, provided is a method of peak detection in an ultrasonic signal, the method including: receiving an ultrasonic signal from an ultrasonic sensor; detecting peaks from the ultrasonic signal; and determining false detection of a peak, among the detected peaks, by using at least one of amplitudes of the detected peaks or a left waveform shape and a right waveform shape of the peak.

The receiving of the ultrasonic signal may include receiving an ultrasonic signal, indicative of a blood flow velocity, from the ultrasonic sensor.

The determining of false detection of the peak may include, in response to an amplitude of a current peak being less than an average of amplitudes of peaks from an immediately preceding peak to the current peak by a predetermined threshold value or greater, determining the current peak as false detection.

The determining of false detection of the peak may include, in response to an amplitude between a reference point and a current peak being less than an amplitude between the reference point and an immediately preceding peak by a predetermined threshold value or greater, determining the current peak as false detection.

The reference point is a point of a minimum amplitude between the current peak and the immediately preceding peak.

The determining of false detection of the peak may include, in response to an amplitude of a current peak being less than an amplitude of an immediately preceding peak by a predetermined threshold value or greater, determining the current peak as false detection.

The determining of false detection of the peak may include: calculating an area of a left region of the peak and an area of a right region of the peak; and in response to the calculated area of the right region being less than the calculated area of the left region by a predetermined threshold value or greater, determining the peak as false detection.

The determining of false detection of the peak may include: calculating a first average slope of a left region of the peak and a second average slope of to right region of the peak; and in response to the second average slope being greater than the first average slope by a predetermined threshold value or greater, determining the peak as false detection.

The determining of false detection of the peak may include determining false detection for a first detected peak or for a peak in a predetermined region at a start of measurement of the ultrasonic signal.

The determining of false detection of the peak may include determining false detection of a current peak by further using a time interval between the current peak and an immediately preceding peak among the detected peaks.

The determining of false detection of the peak may include, in response to the calculated time interval being less than or equal to a predetermined threshold value, determining the current peak as false detection.

The determining of false detection of the peak may include, in response to the calculated time interval being less than a time interval between previous peaks by a predetermined threshold value or greater, determining the current peak as false detection.

According to an aspect of an example embodiment of the disclosure, provided is an apparatus for estimating bio-information by using an ultrasonic signal, the apparatus including: an ultrasonic sensor configured to acquire an ultrasonic signal from an object; and a processor configured to detect peaks from the acquired ultrasonic signal, and to determine false detection of a peak, among the detected peaks, by using at least one of amplitudes of the detected peaks or a left waveform shape and a right waveform shape of the peak.

The ultrasonic signal may be a signal indicative of a blood flow velocity, and wherein the apparatus for estimating bio-information may further include an output interface configured to output at least one of the blood flow velocity, the amplitudes of the peaks, the left waveform shape and the right waveform shape of the peak, or a result of false detection of the peak.

In response to an amplitude of a current peak being less than an average of amplitudes of peaks from an immediately preceding peak to the current peak by a predetermined threshold value or greater, the processor may be configured to determine the current peak as false detection.

In response to an amplitude between a reference point and a current peak being less than an amplitude between the reference point and an immediately preceding peak by a predetermined threshold value or greater, the processor may be configured to determine the current peak as false detection.

The reference point may be a point of a minimum amplitude between the current peak and the immediately preceding peak.

The processor may be configured to calculate an area of a left region of the peak and an area of a right region of the peak, and in response to the calculated area of the right region being less than the calculated area of the left region by a predetermined threshold value or greater, the processor may be configured to determine the peak as false detection.

The processor may be configured to calculate a first average slope of a left region of the peak and a second average slope of a right region of the peak, and in response to the second average slope being greater than the first average slope by a predetermined threshold value or greater, the processor may be configured to determine the peak as false detection.

The processor may be configured to determine false detection for a first detected peak or for a peak in a predetermined region at a start of measurement of the ultrasonic signal.

BRIEF DESCRIPTION OF THE DRAWINGS

The above and/or other aspects will become apparent and more readily appreciated from the following description of example embodiments, taken in conjunction with the accompanying drawings.

DETAILED DESCRIPTION

Figure 1:
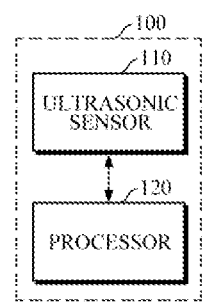
FIG. 1 is a block diagram illustrating an apparatus for estimating bio-information according to an example embodiment of the present disclosure.

Details of example embodiments are included in the following detailed description and drawings. Advantages and features of the present invention, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit for performing at least one function or operation and that may be embodied as hardware, software, or a combination thereof.

Hereinafter, embodiments of an apparatus for estimating bio-information and a method of determining false detection of peaks for estimating bio-information will be described in detail with reference to the accompanying drawings. The apparatus for estimating bio-information according to the embodiments of the present disclosure may be mounted in a terminal, such as a smartphone, a tablet PC, a desktop computer, a laptop computer, etc., or may be manufactured as an independent hardware device. In this case, the independent hardware device may be a wearable device worn by a user, such as a wristwatch-type wearable device, a bracelet-type wearable device, a wristband-type wearable device, a glasses-type wearable device, a headband-type wearable device, etc., but is not limited thereto.

FIG. 1 is a block diagram illustrating an apparatus for estimating bio-information according to an embodiment of the present disclosure.

Referring to FIG. 1, an apparatus 100 for estimating bio-information includes an ultrasonic sensor 110 and a processor 120. The ultrasonic sensor 110 and the processor 120 may be integrally formed with each other in a single hardware device, or may be separately formed in two or more hardware devices.

The ultrasonic sensor 110 may transmit ultrasonic waves to an object under the control of the processor 120 and may receive reflection waves reflected from the object to acquire an ultrasonic signal from the object. In this case, the ultrasonic signal acquired by the ultrasonic sensor 110 may be a bio-signal reflected from the human body, and the bio-signal may indicate a blood flow velocity of the object. The ultrasonic sensor 110 may include an ultrasonic transducer for converting an electrical signal into an ultrasonic signal or converting an ultrasonic signal into an electrical signal. The ultrasonic transducer, having ultrasonic elements arranged in a linear one-dimensional array or in a two-dimensional array, may acquire the ultrasonic images. The ultrasonic elements may be formed with piezoelectric elements.

The processor 120 may be electrically connected to the ultrasonic sensor 110. In response to a request for estimating bio-information, the processor 120 may control the ultrasonic sensor 110, and the ultrasonic sensor 110 may acquire a bio-signal from the object. The request for estimating bio-information may be input from a user or may be generated at predetermined intervals.

Upon receiving the bio-signal from the ultrasonic sensor 110, the processor 120 may perform preprocessing, such as filtering for removing noise from the bio-signal, amplifying the bio-signal, converting the bio-signal into a digital signal, smoothing the bio-signal, and the like.

Upon receiving the bio-signal from the ultrasonic sensor 110, the processor 120 may detect peaks from the bio-signal, and may determine false detection of the detected peaks. For example, the processor 120 may detect peaks from the bio-signal and may determine false detection of the detected peaks by combining at least one or more of the following: a time interval between a current peak and an immediately preceding peak; amplitudes of the current peak and the immediately preceding peak; left and right waveform shapes of a peak; and peak occurrence positions.

Figure 2:
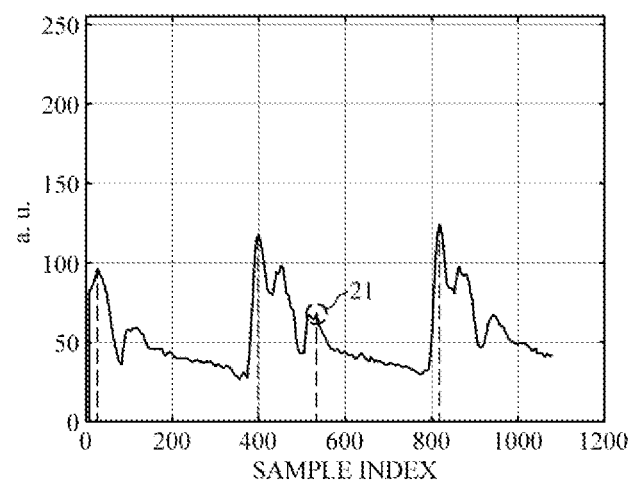
FIG. 2 is a diagram explaining occurrence of false detection during measurement of peaks in a bio-signal.

FIG. 2 is a diagram explaining occurrence of false detection during measurement of peaks in a bio-signal. In this case, the bio-signal may indicate a blood flow velocity.

Generally, peaks may be falsely detected due to different shapes of bio-signal waveforms in an individual or between individuals. For example, referring to FIG. 2, straight lines in a vertical axis direction indicate results of detecting peak positions for each beat duration according to a predetermined algorithm. In this case, the peak indicates a maximum amplitude value in a predetermined region (e.g., heartbeat period) of an envelope detected from an ultrasonic signal. For a second beat duration, unlike other beat durations, a local peak 21 is detected which appears during a diastolic phase of the heart, and which may be determined as false detection. In the case where the bio-signal peak is used as a feature value, it is required to determine the local peak 21 as false detection and to remove or correct the local peak 21 in order to improve the accuracy of estimation. In this case, the X-axis in FIG. 2 represents time, and the Y-axis represents blood flow velocity (m/s) which is a signal intensity, and values on the Y-axis may vary according to a predetermined criterion.

The processor 120 according to an example embodiment may detect peaks from the bio-signal and may determine false detection of the peaks by using, for example, a time interval between a current peak and an immediately preceding peak among the detected peaks.

Figure 3A:
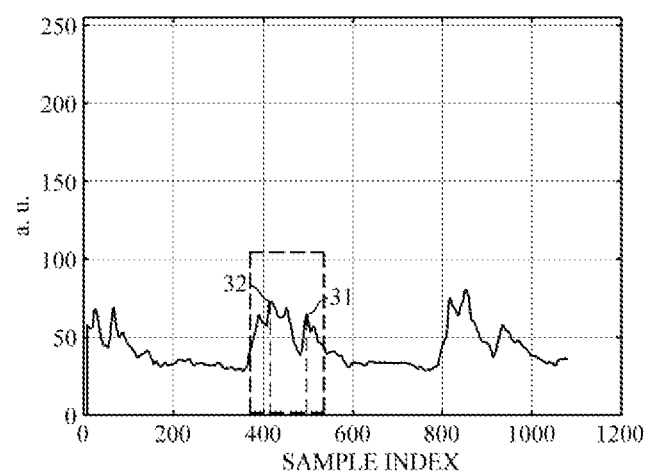
FIGS. 3A and 3B are diagrams explaining examples of determining false detection of a peak by using a time interval between a current peak and an immediately preceding peak, according to example embodiments of the present disclosure.

FIG. 3A is a diagram explaining an example of determining false detection of peaks by using a time interval between a current peak and an immediately preceding peak, according to an embodiment of the present disclosure.

For example, the processor 120 may calculate a time interval between a current peak and an immediately preceding peak, and if the calculated time interval is less than or equal to a predetermined threshold value, the processor 120 may determine the current peak as false detection.

Referring to FIG. 3A, a current peak 31 and an immediately preceding peak 32 among the detected peaks are shown in a dotted line box. For example, if a range of measurable beats per minute (BPM) is between 30 bpm to 200 bpm, a threshold value for a minimum allowable beat duration may be determined to be 0.3 seconds (1*60 (sec)/200 (bpm)). The processor 120 may calculate a time interval between the current peak 31 and the immediately preceding peak 32, and if the calculated time interval is less than or equal to the threshold value of 0.3 seconds, the processor 120 may determine that the current peak 31 is detected in an abnormal waveform and may determine the current peak 31 as false detection. Here, the threshold value may be set to other values depending on an apparatus or an algorithm, and is not limited thereto.

Figure 3B:
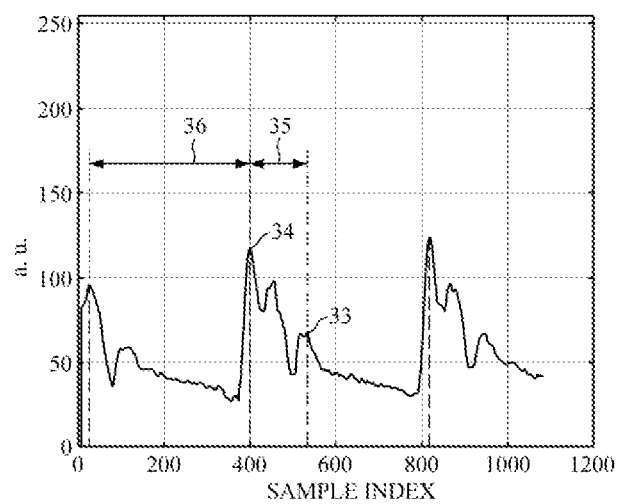

FIG. 3B is a diagram explaining an example of determining false detection of peaks by using a time interval between a current peak and an immediately preceding peak, according to an embodiment of the present disclosure.

For example, the processor 120 may calculate a time interval between a current peak and an immediately preceding peak, and if the calculated time interval is less than or equal to a time interval between other previous peaks by a predetermined threshold value (that is, if the calculated time interval is less than or equal to a time interval value obtained by reducing a time interval between other previous peaks by a predetermined threshold value), the processor 120 may determine the current peak as false detection.

Referring to FIG. 3B, the processor 120 calculates an inter-beat interval (IBI) 35, which is a time interval between the current peak 33 and the immediately preceding peak 34, and an IBI 36, which is a time interval between the previous peaks. If the calculated IBI 35 is a value less than or equal to a predetermined threshold value, for example, a value corresponding to 40% or less of the IBI 36 (that is, if the calculated IBI 35 is less than the IBI 36 by a predetermined threshold value or more), the processor 120 may determine that the current peak 33 is detected in an abnormal waveform and may determine the current peak 33 as false detection. Here, the threshold value may be set to other values depending on an apparatus or an algorithm, and is not limited thereto.

Further, the processor 120 may detect peaks from the bio-signal and may determine false detection of the peaks by using amplitudes of a current peak and an immediately preceding peak among the detected peaks.

Figure 4A:
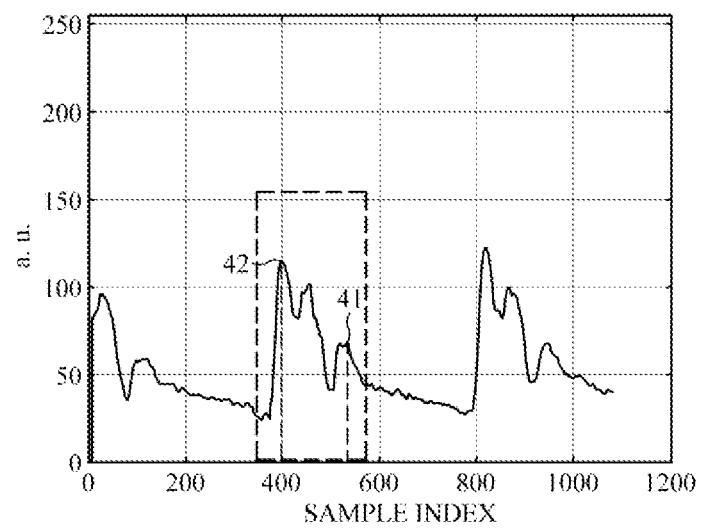
FIGS. 4A and 4B are diagrams explaining examples of determining false detection of a peak by using amplitudes of a current peak and an immediately preceding peak, according to example embodiments of the present disclosure.

FIG. 4A is a diagram explaining an example of determining false detection of peaks by using amplitudes of a current peak and an immediately preceding peak, according to an embodiment of the present disclosure.

For example, if an amplitude of the current peak is less than an amplitude of the immediately preceding peak by a predetermined threshold value or more (that is, if an amplitude of the current peak is less than or equal to an amplitude value obtained by reducing an amplitude of the immediately preceding peak by a predetermined threshold value), the processor 120 may determine the current peak as false detection. Further, if the amplitude of the current peak is less than or equal to an average of the amplitudes of peaks from the immediately preceding peak to the current peak that is reduced by a predetermined threshold value, the processor 120 may determine the current peak as false detection. Hereinafter, the expression "A being less than or equal to B by a predetermined threshold value" refers to the case where A is less than B by a predetermined threshold value of more.

Referring to FIG. 4A, a current peak 41 and an immediately preceding peak 42 among the detected peaks are shown in a dotted line box. For example, if an amplitude of the current peak 41 is 70% or less of an amplitude of the immediately preceding peak 42, the processor 120 may determine that the current peak 41 is detected in an abnormal waveform and may determine the current peak 41 as false detection. In addition, if the amplitude of the current peak 41 is 100% or less of an average of signal amplitudes in a region between the current peak 41 and the immediately preceding peak 42, the processor 120 may determine that the current peak 41 is detected in an abnormal waveform and may determine the current peak 41 as false detection. However, a value corresponding to 70% of the amplitude or 100% of the average of the amplitudes, which is the threshold value, may vary depending on an apparatus or an algorithm, and is not limited thereto.

Further, if an amplitude between a reference point and the current peak is less than or equal to an amplitude between the reference point and the immediately preceding peak by a predetermined threshold value, the processor 120 may determine the current peak as false detection. In this case, the reference point may be a point of minimum amplitude between the current peak and the immediately preceding peak, but is not limited thereto.

Figure 4B:
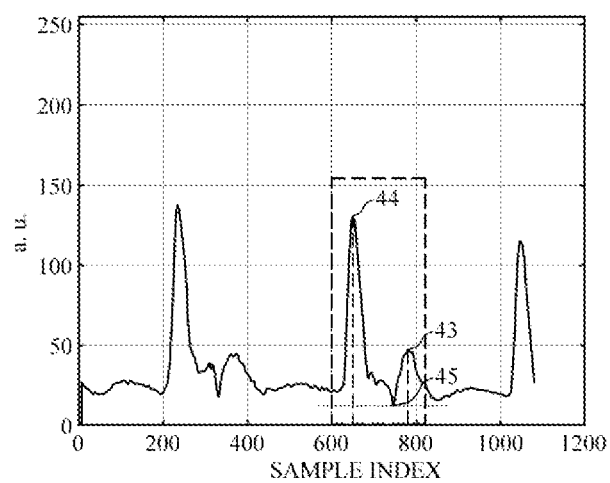

FIG. 4B is a diagram explaining an example of determining false detection of peaks by using amplitudes of a current peak and an immediately preceding peak, according to another embodiment of the present disclosure.

Referring to FIG. 4B, a current peak 43 and an immediately preceding peak 44 among the detected peaks are shown in a dotted line box, and a reference point 45 corresponding to the point of minimum amplitude is located between the current peak 43 and the immediately preceding peak 44. If an amplitude between the reference point 45 and the current peak 43 is 40% or less of an amplitude between the reference point 45 and the immediately preceding peak 44, the processor 120 may determine that the current peak 41 is detected in an abnormal waveform and may determine the current peak 41 as false detection. However, the reference point 45, which is the minimum point, and a value corresponding to 40% of the amplitude between the reference point 45 and the immediately preceding peak 44, which is the threshold value, may vary depending on an apparatus or an algorithm, and are not limited thereto.

In addition, when determining false detection of peaks by using the amplitudes of the current peak and the immediately preceding peak, the processor 120 may combine two or more conditions to improve the accuracy. For example, the processor 120 may combine the case where the amplitude of the current peak is 70% or less of the amplitude of the immediately preceding peak with the case where the amplitude of the current peak is 100% or less of the average of the amplitudes of peaks from the immediately preceding peak to the current peak, and if the current peak corresponds to the combination of the cases (that is, satisfies both conditions of the cases), the processor 120 may determine the current peak as false detection. In addition, the processor 120 may combine the case where the amplitude of the current peak is 70% or less of the amplitude of the immediately preceding peak with the case where the amplitude between the current peak and the reference point, which corresponds to the minimum point between the current peak and the immediately preceding peak, is 40% or less of the amplitude between the reference point and the immediately preceding peak, and if the current peak corresponds to the combination of the cases, the processor 120 may determine the current peak as false detection.

In addition, the processor 120 may detect peaks from the bio-signal and may determine false detection of the peaks by using left and right waveform shapes of the peaks. Based on a general physiological phenomenon that a speed of the heart's contraction is faster than the heart's dilation, the processor 120 may determine false detection using waveform shapes.

Figure 5A:
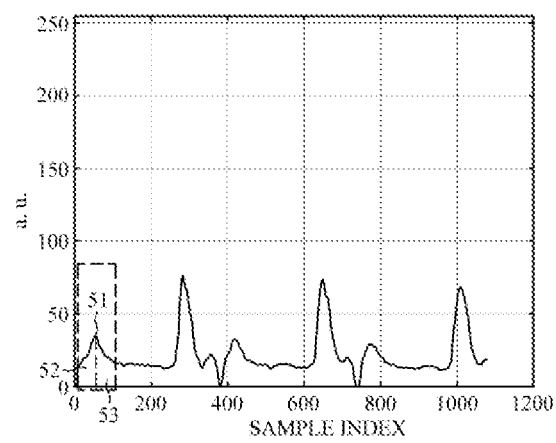
FIGS. 5A and 5B are diagrams explaining an example of determining false detection of a peak by using left and right waveform shapes of the peak, according to example embodiments of the present disclosure.

FIG. 5A is a diagram explaining an example of determining false detection of peaks by using left and right waveform shapes of a peak, according to an embodiment of the present disclosure.

For example, the processor 120 may calculate areas of predetermined left and right regions of a peak, and if the calculated area of the right region is less than or equal to the calculated area of the left region by a predetermined threshold value, the processor 120 may determine the peak as false detection.

Referring to FIG. 5A, an area 52 of the left region and an area 53 of the right region of a peak 51 are shown in a dotted line box. For example, if the area 53 of the right region is 110% or less of the area 52 of the left region, the processor 120 determines that the peak is detected in an abnormal waveform and may determine the peak 51 as false detection. However, the threshold value of 110% may vary depending on an apparatus or an algorithm, and is not limited thereto.

Figure 5B:
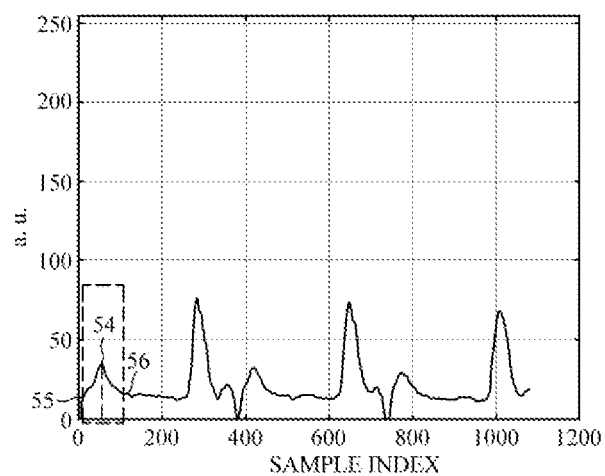

FIG. 5B is a diagram explaining an example of determining false detection of peaks by using left and right waveform shapes of a peak, according to an embodiment of the present disclosure.

For example, the processor 120 may calculate a first average slope of the left region and a second average slope of the right region of a peak, and if the second average slope is greater than or equal to the first average slope by a predetermined threshold value, the processor 120 may determine the peak as false detection.

Referring to FIG. 5B, a dotted line box indicates a predetermined region, and a detected peak 54, and an initial start point 55 located on the left side of the peak 54, and an end point 56 are shown in the dotted line box. The processor 120 may calculate the first average slope by using the peak 54 and the start point 55 and may calculate the second average slope by using the peak 54 and the end point 56. For example, if the calculated second average slope is 90% or more of the first average slope, the processor 120 determines that the peak 54 is detected in an abnormal waveform and may determine the peak 54 as false detection. However, a value corresponding to 90% of the slope, which is the threshold value, may vary depending on an apparatus or an algorithm, and is not limited thereto.

There may be a case in which the accuracy in determining the false detection may be reduced in a general detection region due to various signal shapes and the presence of noise. In such a case, the false detection may be determined based on the waveform shapes as illustrated in FIGS. 5A and 5B. Accordingly, the determination of false detection based on the waveform shapes may be applied to a first detected peak or peaks in a predetermined region at the initial stage of measurement, in which it is difficult to determine false detection by using time intervals or amplitudes of the detected peaks.

Furthermore, the processor 120 may detect peaks from the bio-signal and may determine false detection of the peaks by using peak occurrence positions.

Figure 6:
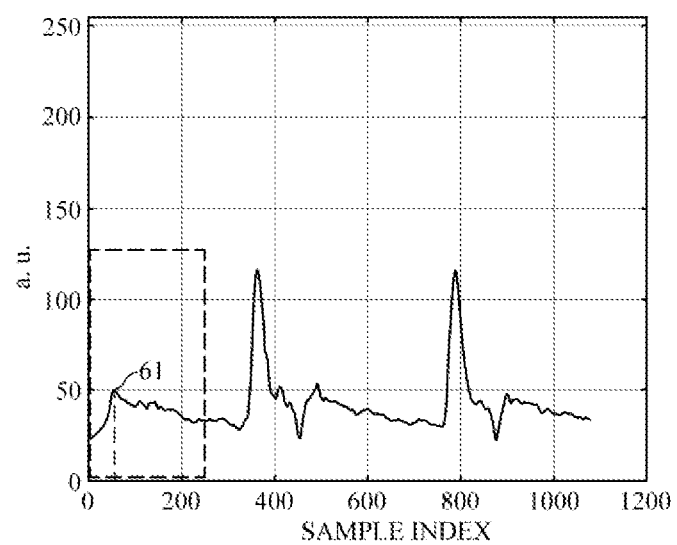
FIG. 6 is a diagram explaining an example of determining false detection of a peak by using peak occurrence positions, according to an example embodiment of the present disclosure.

FIG. 6 is a diagram explaining an example of determining false detection of peaks by using peak occurrence positions, according to an embodiment of the present disclosure.

For example, if a peak is detected in a predetermined start region or end region, the processor 120 may determine the peak as false detection. That is, if the position of the detected peak is biased to a start portion or an end portion of the entire detection region, the processor 120 may determine that the peak is detected in an abnormal waveform.

Referring to FIG. 6, the detected peak 61 is shown in a dotted line box indicating a predetermined region from a start point. For example, if the peak 61 is detected in a region, indicated by the dotted line box, which corresponds to 20% of the detection region from the start point, the processor 120 may determine that the peak is detected in an abnormal waveform and may determine the peak as false detection. In addition to the region corresponding to 20% of the detection region from the start point, the processor 120 may also determine the peak, which is detected in a region corresponding to 20% of the detection region from the end point, as false detection. The threshold value of 20% may vary depending on an apparatus or an algorithm, and is not limited thereto. Generally, at the initial stage of signal measurement, it is difficult to determine false detection by using the time interval between the current peak and the immediately preceding peak or the amplitudes thereof. Accordingly, in this case, the method of determining false detection of peaks by using the peak occurrence positions according to an example embodiment of FIG. 6 may be used.

In order to increase the accuracy in determining false detection, the processor 120 may determine false detection of peaks by combining two or more of time intervals, amplitudes, waveform shapes, and occurrence positions of the detected peaks. For example, the processor 120 may calculate a time interval between the current peak and the immediately preceding peak, and may combine a case where the calculated time interval is 0.3 seconds or less with a case where an amplitude of the current peak is 70% or less of an amplitude of the immediately preceding peak. If the current peak corresponds to a combination of the cases, the processor 120 may determine that the current peak is detected in an abnormal waveform and may determine the current peak as false detection.

Various embodiments of false detection are described above, but the present disclosure is not limited thereto, and false detection of peaks may be determined by using a combination of two or more of the above embodiments or various other embodiments not described herein.

The processor 120 may estimate bio-information based on a result of false detection.

The processor 120 may estimate bio-information based on the detected peaks by excluding a peak determined as false detection, and by using a pre-defined bio-information estimation model. For example, the processor 120 may estimate bio-information by using, as features, an amplitude value itself at the peak or a value obtained by processing the amplitude value, for example, a value obtained by adding or subtracting a predetermined value to or from the amplitude value or by multiplying or dividing the amplitude value by a predetermined value, and the like according to the type of bio-information, unusual circumstances of a user, and the like, and by using a pre-defined bio-information estimation model. In this case, the bio-information estimation model may be defined as various linear or non-linear combination functions, such as addition, subtraction, division, multiplication, logarithmic value, regression equation, and the like, with no specific limitation. Here, the bio-information may include information, such as arrhythmia, blood pressure, vascular age, arterial stiffness, aortic pressure waveform, vascular compliance, stress index, fatigue level, and the like.

In addition, if a number of peaks determined as false detection is greater than or equal to a predetermined threshold value, the processor 120 may output guide information for remeasuring peaks, ending the measurement, extending a measurement time, etc., or may perform these operations.

Further, upon determining that peaks occur at irregular intervals based on the determination of false detection, the processor 120 may determine that a health condition of an object corresponds to arrhythmia, and may output information thereon.

Figure 7:
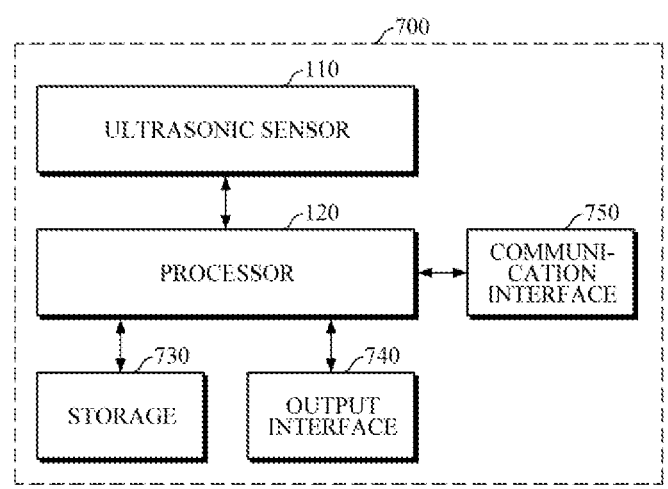
FIG. 7 is a block diagram illustrating an apparatus for estimating bio-information according to another example embodiment of the present disclosure.

FIG. 7 is a block diagram illustrating an apparatus for estimating bio-information according to another embodiment of the present disclosure.

Referring to FIG. 7, the apparatus 700 for estimating bio-information may include the ultrasonic sensor 110, the processor 120, a storage 730, an output interface 740, and a communication interface 750. In this case, the ultrasonic sensor 110 and the processor 120 are the same as the ultrasonic sensor 110 and the processor 120 of the embodiment in FIG. 1, such that a detailed description thereof will be omitted.

The communication interface 750 may communicate with an external device by using wired or wireless communication techniques under the control of the processor 120, and may transmit and receive various data with the external device. For example, the communication interface 750 may transmit a bio-information estimation result to the external device, and may receive a variety of reference information required for estimating bio-information from the external device. For example, the reference information may include a reference blood pressure, a reference heart rate, a bio-information estimation equation, a bio-information estimation period, as well as user characteristic information, such as a user's age, gender, health condition, and the like. However, the reference information is not limited thereto. In this case, the external device may include an information processing device, such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, 5G, and 6G communications, and the like. However, this is merely exemplary and is not intended to be limiting.

The output interface 740 may output results processed by the ultrasonic sensor 110 and the processor 120. For example, the output interface 740 may visually output the blood flow velocity, amplitudes and left and right waveform shapes of peaks, result of false detection of peaks, or an estimated bio-information value through a display module. Alternatively, the output interface 740 may non-visually output the estimated bio-information value by voice, vibrations, tactile sensation, and the like using a speaker module, a haptic module, or the like. In this case, by dividing a display area into two or more areas according to a setting, the output interface 740 may output an ultrasonic signal graph used for estimating bio-information, a bio-information estimation result, and the like in a first area, and may output a bio-information estimation history in the form of graphs and the like in a second area. In this case, if the estimated bio-information value falls outside a normal range, the output interface 740 may output warning information in various manners, such as highlighting an abnormal value in red and the like, displaying the abnormal value along with a normal range, outputting a voice warning message, adjusting a vibration intensity, and the like.

The storage 730 may store processing results of the ultrasonic sensor 110 and the processor 120. Further, the storage 730 may store a variety of reference information required for estimating bio-information.

In this case, the storage 730 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 8:
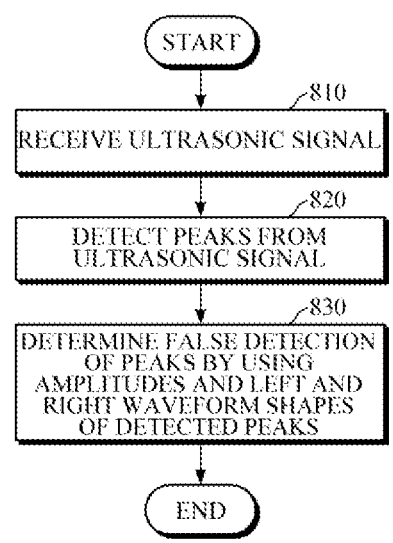
FIG. 8 is a flowchart illustrating a method of determining false detection of a peak in a bio-signal according to an example embodiment of the present disclosure.

FIG. 8 is a flowchart illustrating a method of determining false detection of peaks in a bio-signal according to an embodiment of the present disclosure. The method of FIG. 8 is an example of a method of determining false detection of peaks of a bio-signal performed by the aforementioned apparatuses 100 and 700 for estimating bio-information, which is described in detail above and thus will be briefly described below.

First, the apparatus for estimating bio-information may receive an ultrasonic bio-signal measured by the ultrasonic sensor from an object in 810.

Then, the apparatus for estimating bio-information may detect peaks from the received ultrasonic signal in 820. For example, the apparatus for estimating bio-information may detect the peaks by sliding in a predetermined detection region over time using a predetermined peak detection algorithm. In this case, the ultrasonic signal may indicate a blood flow velocity.

Subsequently, the apparatus for estimating bio-information may determine false detection of the peaks by combining at least one or more of amplitudes and left and right waveform shapes of the detected peaks in 830.

For example, the apparatus for estimating bio-information may determine false detection of peaks by using amplitudes of the current peak and the immediately preceding peak among the detected peaks.

For example, if an amplitude of the current peak is less than or equal to an amplitude of the immediately preceding peak by a predetermined threshold value, the apparatus for estimating bio-information may determine the current peak as false detection. In addition, if the amplitude of the current peak is less than or equal to an average of the amplitudes of peaks from the immediately preceding peak to the current peak by a predetermined threshold value, the apparatus for estimating bio-information may determine the current peak as false detection.

For example, if the amplitude of the current peak is 70% or less of the amplitude of the immediately preceding peak, the apparatus for estimating bio-information may determine that the current peak is detected in an abnormal waveform and may determine the current peak as false detection. In addition, if the amplitude of the current peak is 100% or less of an average of the amplitudes of peaks from the immediately preceding peak to the current peak, the apparatus for estimating bio-information may determine that the current peak is detected in an abnormal waveform and may determine the current peak as false detection.

Further, if an amplitude between a reference point and the current peak is less than or equal to an amplitude between the reference point and the immediately preceding peak by a predetermined threshold value, the apparatus for estimating bio-information, the apparatus for estimating bio-information may determine the current peak as false detection. For example, if the amplitude between the current peak and the reference point, corresponding to a minimum point between the current peak and the immediately preceding peak, is 40% or less of the amplitude between the reference point and the immediately preceding peak, the apparatus for estimating bio-information may determine that the current peak is detected in an abnormal waveform and may determine the current peak as false detection.

Furthermore, when determining false detection of peaks by using the amplitudes of the current peak and the immediately preceding peak, the apparatus for estimating bio-information may combine two or more conditions to improve accuracy. For example, the apparatus for estimating bio-information may combine a case where the amplitude of the current peak is 70% or less of the amplitude of the immediately preceding peak with a case where the amplitude of the current peak is 100% or less of the average of signal amplitudes in a region between the current peak and the immediately preceding peak, and if the current peak corresponds to a combination of the cases, the apparatus for estimating bio-information may determine that the current peak is detected in an abnormal waveform and may determine the current peak as false detection. In addition, the apparatus for estimating bio-information may combine a case where the amplitude of the current peak is 70% or less of the amplitude of the immediately preceding peak with a case where the amplitude between the current peak and the reference point, corresponding to a minimum point between the current peak and the immediately preceding peak, is 40% or less of the amplitude between the reference point and the immediately preceding peak, and if the current peak corresponds to a combination of the cases, the apparatus for estimating bio-information may determine the current peak as false detection.

The apparatus for estimating bio-information may determine false detection of peaks by using left and right waveform shapes of a peak.

For example, the apparatus for estimating bio-information may calculate areas of predetermined left and right regions of a peak, and if the calculated area of the right region is less than or equal to the calculated area of the left region by a predetermined threshold value, the apparatus for estimating bio-information may determine the peak as false detection. For example, if the area of the right region is 110% or less of the area of the left region of the detected peak, the apparatus for estimating bio-information determines that the peak is detected in an abnormal waveform and may determine the peak as false detection.

Further, the apparatus for estimating bio-information may calculate a first average slope of the left region and a second average slope of the right region of a peak, and if the second average slope is greater than or equal to the first average slope by a predetermined threshold value, the apparatus for estimating bio-information may determine the peak as false detection. For example, with respect to the peak, the apparatus for estimating bio-information may calculate the first average slope by using the peak and a start point, and may calculate the second average slope by using the peak and an end point, and if the calculated second average slope is 90% or more of the first average slope, the apparatus for estimating bio-information may determine that the peak is detected in an abnormal waveform and may determine the peak as false detection. In this case, determination of false detection based on waveform shapes may be performed on a first detected peak or peaks in a predetermined region at the start of measurement of the ultrasonic signal.

In addition, the apparatus for estimating bio-information may determine false detection of the peaks by using the time interval between the current peak and the immediately preceding peak among the detected peaks.

For example, the apparatus for estimating bio-information may calculate the time interval between the current peak and the immediately preceding peak, and if the calculated time interval is less than or equal to a predetermined threshold value, the apparatus for estimating bio-information may determine the current peak as false detection. For example, if the calculated time interval between the current peak and the immediately preceding peak is 0.3 seconds or less which is a threshold value, the apparatus for estimating bio-information may determine that the current peak is detected in an abnormal waveform and may determine the current peak as false detection. However, the threshold value may vary according to an apparatus or an algorithm, and is not limited thereto.

In addition, the apparatus for estimating bio-information may calculate the time interval between the current peak and the immediately preceding peak, and if the calculated time interval is less than or equal to a time intervals between previous peaks by a predetermined threshold value, the apparatus for estimating bio-information may determine the current peak as false detection. For example, if an inter-beat interval (IBI) between the current peak and the preceding peak is a value less than or equal to 40% of a previous IBI, which is a predetermined threshold value, the apparatus for estimating bio-information may determine that the current peak is detected in an abnormal waveform and may determine the current peak as false detection.

Further, the apparatus for estimating bio-information may determine false detection of peaks by using peak occurrence positions. That is, if a peak is detected in a predetermined start region or end region, the apparatus for estimating bio-information may determine the peak as false detection. For example, if the peak is detected in a region corresponding to 20% of the detection region from the start point, the apparatus for estimating bio-information may determine that the peak is in an abnormal waveform and may determine the peak as false detection. Further, if a peak is detected in a region corresponding to 20% of the detection region from the end point, in addition to the region corresponding to 20% of the detection region from the start point, the apparatus for estimating bio-information may determine the peak as false detection.

The apparatus for estimating bio-information may combine two or more of the time interval, amplitudes, waveform shapes, and occurrence positions of the detected peaks to improve the accuracy in determining false detection. For example, the apparatus for estimating bio-information may calculate the time interval between the current peak and the immediately preceding peak, and by combining a case where the calculated time interval is 0.3 seconds or less with a case where the amplitude of the current peak is 70% or less of the amplitude of the immediately preceding peak, if the current peak corresponds to a combination of the cases, the apparatus for estimating bio-information determines that the current peak is detected in an abnormal waveform and may determine the current peak as false detection.

Various embodiments of determining false detection are described above, but the present disclosure is not limited thereto, and false detection of peaks may be determined by combining two or more of the above embodiments or by using various other examples not described herein.

Figure 9:
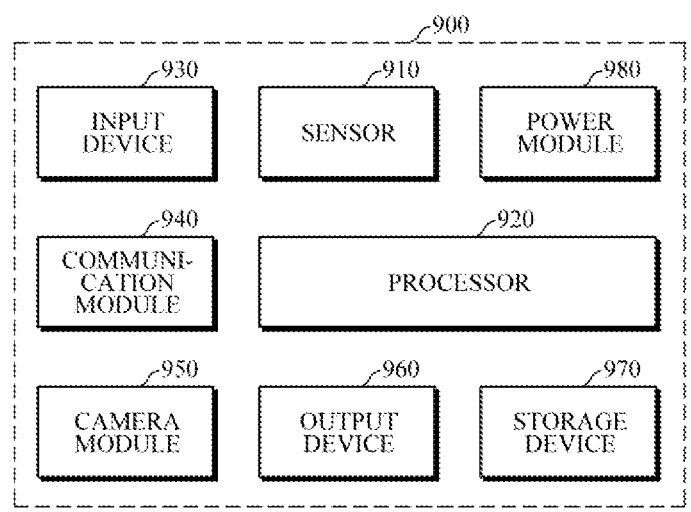
FIG. 9 is a block diagram illustrating an electronic device including an apparatus for estimating bio-information according to an example embodiment of the present disclosure.

FIG. 9 is a block diagram illustrating an electronic device including the apparatus 100 or 700 for estimating bio-information.

The electronic device according to the embodiment of the present disclosure may include, for example, various types of wearable devices, e.g., a smart watch, a smart band, smart glasses, smart earphones, a smart ring, a smart patch, and a smart necklace, and a mobile device such as a smartphone, a tablet PC, etc., or home appliances or various Internet of Things (IoT) devices (e.g., home IoT device, etc.) based on Internet of Things (IoT) technology.

Referring to FIG. 9, the electronic device 900 may include a sensor 910, a processor 920, an input device 930, a communication module 940, a camera module 950, an output device 960, a storage device 970, and a power module 980. All the components of the electronic device 900 may be integrally mounted in a specific device or may be distributed in two or more devices.

The sensor 910 may include a pulse wave sensor, in addition to the ultrasonic sensor 110 of the aforementioned apparatuses 100 and 700 for estimating bio-information.

The pulse wave sensor may measure a pulse wave signal, including a photoplethysmography (PPG) signal, from the object. The pulse wave sensor may include light sources for emitting light onto the object to detect an optical signal, and detectors for detecting light scattered or reflected from body tissue, such as the skin surface, blood vessels, and the like, of the object after the light is emitted by the light sources. The light source may include a light emitting diode (LED), a laser diode (LD), a phosphor, etc., but is not limited thereto. The detector may include a photo diode, a photo transistor (PTr), or an image sensor (e.g., complementary metal-oxide semiconductor (CMOS) image sensor), etc., but is not limited thereto. The pulse wave sensor may have various types of structures, such as a structure having a plurality of light sources and one detector, or a structure having an array of pairs of light sources and detectors, etc., with no specific limitation. In this case, the object may be a body part which comes into contact with or is adjacent to the pulse wave sensor, and at which pulse waves may be easily measured. For example, the object may be the skin surface of the wrist that is adjacent to the radial artery, or an upper part of the wrist where veins or capillaries are located. However, the object is not limited thereto and may be peripheral parts of the body, such as fingers, toes, and the like where blood vessels are densely located.

The processor 920 may execute programs, stored in the storage device 970, to control components connected to the processor 920, and may perform various data processing or computation. The processor 920 may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), etc., which is operable independently from, or in conjunction with, the main processor.

The processor 920 may include the processor of the aforementioned apparatuses 100 and 700 for estimating bio-information. For example, in response to a user's request for estimating bio-information, the processor 920 may transmit a control signal to the sensor 910, and may estimate bio-information by using the bio-signal (e.g., blood flow velocity) received from the sensor 910.

Upon receiving a bio-signal from the sensor 910, the processor 920 may detect peaks from the bio-signal, may determine false detection of the peaks by combining at least one or more of a time interval between a current peak and an immediately preceding peak among the detected peaks, left and right waveform shapes of a peak, and peak occurrence positions, and may determine a user's health condition based on the determination. For example, the processor 920 may estimate bio-information by using, as features, the detected peaks except a peak determined as false detection, and by using a pre-defined bio-information estimation model, and may determine the user's health condition based on the estimation.

The input device 930 may receive a command and/or data to be used by each component of the electronic device 900, from a user and the like. The input device 930 may include, for example, a microphone, a mouse, a keyboard, or a digital pen (e.g., a stylus pen, etc.).

The communication module 940 may support establishment of a direct (e.g., wired) communication channel and/or a wireless communication channel between the electronic device 900 and other electronic device, a server, or the sensor 910 within a network environment, and performing of communication via the established communication channel. The communication module 940 may include one or more communication processors that are operable independently from the processor 920 and supports a direct communication and/or a wireless communication.

The communication module 940 may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device 900 in a communication network by using subscriber information (e.g., international mobile subscriber identity (IMSI), etc.) stored in a subscriber identification module.

The camera module 950 may capture still images or moving images. The camera module 950 may include a lens assembly having one or more lenses, image sensors, image signal processors, and/or flashes. The lens assembly included in the camera module 950 may collect light emanating from a subject to be imaged.

The output device 960 may visually and/or non-visually output data generated or processed by the electronic device 900. The output device 960 may include a sound output device, a display device, an audio module, and/or a haptic module.

The sound output device may output sound signals to the outside of the electronic device 900. The sound output device may include a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device 900. The display device may include, for example, a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch.

The audio module may convert a sound into an electrical signal or vice versa. The audio module may obtain the sound via the input device, or may output the sound via the sound output device, and/or a speaker and/or a headphone of another electronic device directly or wirelessly connected to the electronic device 900.

The haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The storage device 970 may store driving conditions required for driving the sensor 910, and various data required for other components of the electronic device 900. The various data may include, for example, software and input data and/or output data for a command related thereto. The storage device 970 may include a volatile memory and/or a non-volatile memory.

The power module 980 may manage power supplied to the electronic device 900. The power management module may be implemented as least part of, for example, a power management integrated circuit (PMIC). The power module 980 may include a battery, which may include a primary cell which is not rechargeable, a secondary cell which is rechargeable, and/or a fuel cell.

Figure 10:
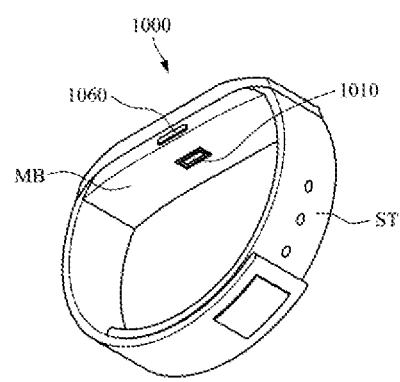
FIG. 10 is a diagram illustrating an example of an electronic device implemented as a smart watch wearable device according to an example embodiment of the present disclosure.
Figure 11:
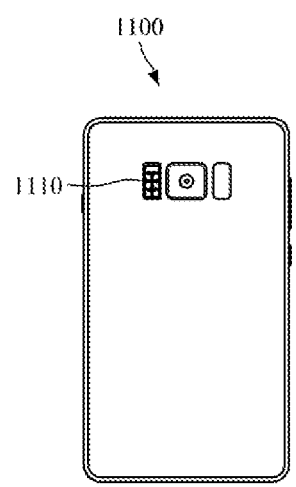
FIG. 11 is a diagram illustrating an example of an electronic device implemented as a mobile device according to an example embodiment of the present disclosure.
Figure 12:
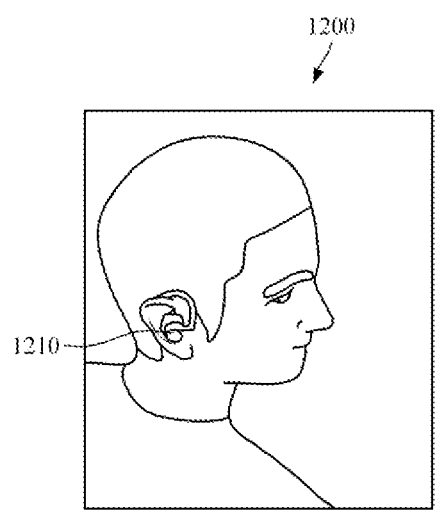
FIG. 12 is a diagram illustrating an example of an electronic device implemented as an ear-wearable device according to an example embodiment of the present disclosure.

FIGS. 10 to 12 are diagrams illustrating examples of structures of the electronic device 900 of FIG. 9 including the apparatus for estimating bio-information. Examples of the electronic device may include not only a smartphone, but also a smart watch, a smart band, smart glasses, a smart necklace, and an ear-wearable device, but the electronic device is not limited thereto.

Referring to FIG. 10, the electronic device 900 including the apparatus for estimating bio-information according to an example embodiment may be implemented as a smart watch wearable device 1000, which includes a main body MB and a wrist strap ST.

The main body MB may be formed in various shapes, and a battery may be embedded in the main body MB and/or the strap ST to supply power to various components of the wearable device. The strap ST may be connected to both ends of the main body to allow the main body to be worn on a user's wrist, and may be flexible so as to be wrapped around the user's wrist. The strap ST may include a first strap and a second strap which are separated from each other. One ends of the first strap and the second strap are connected to both sides of the main body MB, and the other ends thereof may be connected to each other via a fastening means. In this case, the fastening means may be formed as magnetic fastening, Velcro fastening, pin fastening, and the like, but is not limited thereto. Further, the strap ST is not limited thereto, and may be integrally formed as a non-detachable band.

The main body MB may include the apparatus for estimating bio-information. A sensor 1010, a processor, an output interface, a storage, and a communication interface may be mounted in the apparatus for estimating bio-information (e.g., body temperature). However, depending on the size and shape of a form factor and the like, some of the display, the storage, and the communication interface may be omitted. Upon receiving a bio-signal from the sensor 1010, the processor may detect peaks from the bio-signal, and may determine false detection of the peaks. For example, the processor may detect peaks of the bio-signal, may determine false detection of the peaks by combining at least one or more of a time interval between a current peak and an immediately preceding peak among the detected peaks, left and right waveform shapes of a peak, and peak occurrence positions, and may determine a use's health condition based on the determination.

Referring back to FIG. 10, a manipulator 1060 may be formed on a side surface of the main body MB, as illustrated herein. The manipulator 1060 may receive a user's command and may transmit the received command to the processor. In addition, the manipulator 1060 may have a power button to turn on/off the wearable device 1000. A display may be provided on a front surface of the main body MB and may display various application screens, including heart rate information, time information, received message information, and the like.

Referring to FIG. 11, the electronic device 900 including the apparatus for estimating bio-information according to an example embodiment may be implemented as a mobile device 1100 such as a smartphone.

The mobile device 1100 may include a housing and a display panel. The housing may form an exterior of the mobile device 1100. The housing has a first surface, on which a display panel and a cover glass may be disposed sequentially, and the display panel may be exposed to the outside through the cover glass. A sensor 1110, a camera module and/or an infrared sensor, and the like may be disposed on a second surface of the housing. The sensor 1110 may include a pulse wave sensor including one or more light sources and detectors. The sensor 1110 may be mounted on the second surface, but is not limited thereto and may be combined with a fingerprint sensor or a touch panel on the first surface of the housing to form the sensor 1110. When a user transmits a request for estimating bio-information (e.g., body temperature) by executing an application and the like installed in the mobile device 1100, the mobile device 1100 may estimate bio-information by using the sensor 1110 and the processor in the mobile device 1100, and may provide the estimated bio-information value as images and/or sounds to the user.

Referring to FIG. 12, the electronic device 900 including the apparatus for estimating bio-information according to an example embodiment may be implemented as an ear-wearable device 1200.

The ear-wearable device 1200 may include a main body and an ear strap. A user may wear the ear-wearable device 1200 by hanging the ear strap on the auricle. The ear strap may be omitted depending on a shape of the ear-wearable device 1200. The main body may be inserted into the external auditory meatus. A sensor 1210 may be mounted in the main body. Further, the ear-wearable device 1200 may provide the user with a bio-information estimation result as sound, or may transmit the estimation result to an external device, e.g., a mobile device, a tablet PC, etc., through a communication module provided in the main body.

Figure 13:
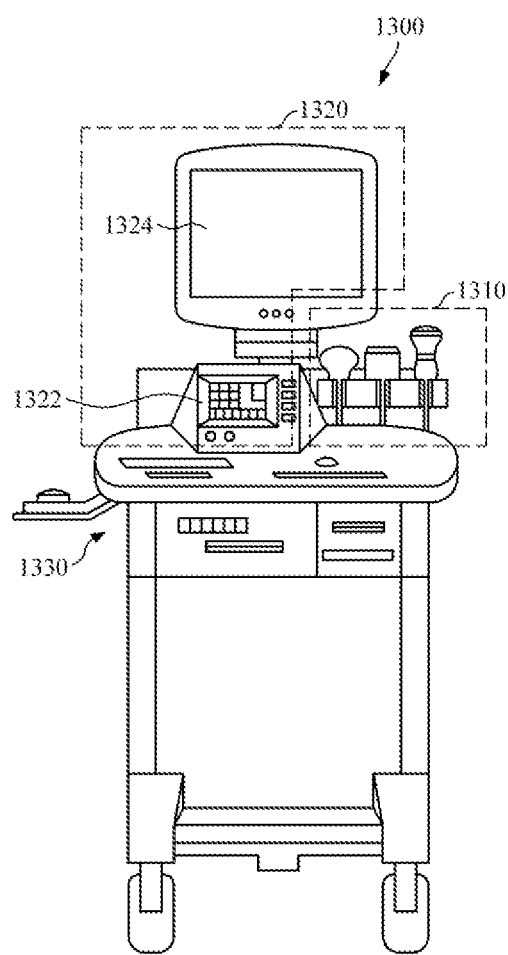
FIG. 13 is a diagram illustrating an ultrasonic diagnostic apparatus including an apparatus for estimating bio-information according to an example embodiment.

FIG. 13 is a diagram illustrating an ultrasonic diagnostic apparatus including an apparatus for estimating bio-information according to an example embodiment.

Referring to FIG. 13, an ultrasonic diagnostic apparatus 1300 may include a probe 1310, a user interface 1320, and a controller 1330. The ultrasonic diagnostic apparatus 1300 may be an apparatus for transmitting an ultrasonic signal to an object and generating an ultrasonic image by using an echo signal reflected from the object, but is not limited thereto. In this case, the ultrasonic image refers to an image of the object which is acquired using ultrasonic waves, and if the object is human body, examples thereof may include organs, such as the liver, heart, uterus, brain, breast, abdomen, etc., or fetus, and the like.

The ultrasonic diagnostic apparatus 1300 may include an apparatus for estimating bio-information according to an example embodiment. For example, the ultrasonic diagnostic apparatus 1300 may include: an ultrasonic sensor configured to acquire an ultrasonic signal from an object; and a processor configured to detect peaks from the ultrasonic signal, and to determine false detection of the peaks by combining at least one or more (or by using one or more) of amplitudes of the detected peaks and left and right waveform shapes of the detected peaks.

The probe 1310 may transmit the ultrasonic signal to the object and may receive an echo signal reflected from the object.

The user interface 1320 may include an input interface 1322 and a display 1324, but is not limited thereto and may also be implemented as one unit having both input and output functions. For example, the user interface 1320 may include all of input/output devices, such as a keyboard, mouse, monitor, touch panel, speaker, etc., which are provided for the ultrasonic diagnostic apparatus 1300, and software for operating the same, but is not limited thereto.

The controller 1330 may control the overall operation of the ultrasonic diagnostic apparatus 1300 including the probe 1310 and the user interface 1320.

The present disclosure may be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments needed for realizing the present invention may be readily deduced by programmers of ordinary skill in the art to which the invention pertains.

At least one of the components, elements, modules or units (collectively "components" in this paragraph) represented by a block in the drawings may be embodied as various numbers of hardware, software and/or firmware structures that execute respective functions described above, according to an example embodiment. According to example embodiments, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Functional aspects of the above exemplary embodiments may be implemented in algorithms that execute on one or more processors. Furthermore, the components represented by a block or processing steps may employ any number of related art techniques for electronics configuration, signal processing and/or control, data processing and the like.

The present disclosure has been described herein with regard to preferred embodiments. However, it will be obvious to those skilled in the art that various changes and modifications may be made without changing technical conception and essential features of the present disclosure. Thus, it is clear that the above-described embodiments are illustrative in all aspects and are not intended to limit the present disclosure.

What is claimed is:

1. A method of peak detection in an ultrasonic signal, the method comprising:
    receiving an ultrasonic signal from an ultrasonic sensor;
    detecting peaks from the ultrasonic signal; and
    determining false detection of a peak, among the detected peaks, by using at least one of amplitudes of the detected peaks or a left waveform shape and a right waveform shape of the peak, and excluding the peak determined as the false detection from the detected peaks.

2. The method of claim 1, wherein the receiving of the ultrasonic signal comprises receiving an ultrasonic signal, indicative of a blood flow velocity, from the ultrasonic sensor.

3. The method of claim 1, wherein the determining of false detection of the peak comprises, in response to an amplitude of a current peak being less than an average of amplitudes of peaks from an immediately preceding peak to the current peak by a predetermined threshold value or greater, determining the current peak as false detection.

4. The method of claim 1, wherein the determining of false detection of the peak comprises, in response to an amplitude between a reference point and a current peak being less than an amplitude between the reference point and an immediately preceding peak by a predetermined threshold value or greater, determining the current peak as false detection.

5. The method of claim 4, wherein the reference point is a point of a minimum amplitude between the current peak and the immediately preceding peak.

6. The method of claim 1, wherein the determining of false detection of the peak comprises, in response to an amplitude of a current peak being less than an amplitude of an immediately preceding peak by a predetermined threshold value or greater, determining the current peak as false detection.

7. The method of claim 1, wherein the determining of false detection of the peak comprises:
    calculating an area of a left region of the peak and an area of a right region of the peak; and
    in response to the calculated area of the right region being less than the calculated area of the left region by a predetermined threshold value or greater, determining the peak as false detection.

8. The method of claim 1, wherein the determining of false detection of the peak comprises:
    calculating a first average slope of a left region of the peak and a second average slope of ta right region of the peak; and
    in response to the second average slope being greater than the first average slope by a predetermined threshold value or greater, determining the peak as false detection.

9. The method of claim 1, wherein the determining of false detection of the peak comprises determining false detection for a first detected peak or for a peak in a predetermined region at a start of measurement of the ultrasonic signal.

10. The method of claim 1, wherein the determining of false detection of the peak comprises determining false detection of a current peak by further using a time interval between the current peak and an immediately preceding peak among the detected peaks.

11. The method of claim 10, wherein the determining of false detection of the peak comprises, in response to the calculated time interval being less than or equal to a predetermined threshold value, determining the current peak as false detection.

12. The method of claim 10, wherein the determining of false detection of the peak comprises, in response to the calculated time interval being less than a time interval between previous peaks by a predetermined threshold value or greater, determining the current peak as false detection.

13. An apparatus for estimating bio-information by using an ultrasonic signal, the apparatus comprising:
    an ultrasonic sensor configured to acquire an ultrasonic signal from an object; and
    a processor configured to detect peaks from the acquired ultrasonic signal, and to determine false detection of a peak, among the detected peaks, by using at least one of amplitudes of the detected peaks or a left waveform shape and a right waveform shape of the peak, and exclude the peak determined as the false detection from the detected peaks.

14. The apparatus of claim 13, wherein the ultrasonic signal is a signal indicative of a blood flow velocity, and
    wherein the apparatus for estimating bio-information further comprises an output interface configured to output at least one of the blood flow velocity, the amplitudes of the peaks, the left waveform shape and the right waveform shape of the peak, or a result of false detection of the peak.

15. The apparatus of claim 13, wherein in response to an amplitude of a current peak being less than an average of amplitudes of peaks from an immediately preceding peak to the current peak by a predetermined threshold value or greater, the processor is configured to determine the current peak as false detection.

16. The apparatus of claim 13, wherein in response to an amplitude between a reference point and a current peak being less than an amplitude between the reference point and an immediately preceding peak by a predetermined threshold value or greater, the processor is configured to determine the current peak as false detection.

17. The apparatus of claim 16, wherein the reference point is a point of a minimum amplitude between the current peak and the immediately preceding peak.

18. The apparatus of claim 13, wherein the processor is configured to calculate an area of a left region of the peak and an area of a right region of the peak, and in response to the calculated area of the right region being less than the calculated area of the left region by a predetermined threshold value or greater, the processor is configured to determine the peak as false detection.

19. The apparatus of claim 13, wherein the processor is configured to calculate a first average slope of a left region of the peak and a second average slope of a right region of the peak, and in response to the second average slope being greater than the first average slope by a predetermined threshold value or greater, the processor is configured to determine the peak as false detection.

20. The apparatus of claim 13, wherein the processor is configured to determine false detection for a first detected peak or for a peak in a predetermined region at a start of measurement of the ultrasonic signal.

* * * * *